US011202810B2

(12) United States Patent
Majeed et al.

(10) Patent No.: US 11,202,810 B2
(45) Date of Patent: Dec. 21, 2021

(54) STABLE PROBIOTIC COMPOSITION FOR THE MANAGEMENT OF LACTOSE INTOLERANCE

(71) Applicants: Muhammed Majeed, Bangalore (IN); Kalyanam Nagabhushanam, East Windsor, NJ (US); Furqan Ali, Bangalore (IN); Sivakumar Arumugam, Bangalore, IN (US); Shaheen Majeed, Springville, UT (US)

(72) Inventors: Muhammed Majeed, Bangalore (IN); Kalyanam Nagabhushanam, East Windsor, NJ (US); Furqan Ali, Bangalore (IN); Sivakumar Arumugam, Bangalore, IN (US); Shaheen Majeed, Springville, UT (US)

(73) Assignee: Sami-Sabinsa Group Limited, Bangalore (IN)

( * ) Notice: Subject to any disclaimer, the term of this patent is extended or adjusted under 35 U.S.C. 154(b) by 101 days.

(21) Appl. No.: 16/372,635

(22) Filed: Apr. 2, 2019

(65) Prior Publication Data
US 2020/0316139 A1    Oct. 8, 2020

(51) Int. Cl.
*A61K 35/742* (2015.01)
*A61P 1/00* (2006.01)
*A61K 38/43* (2006.01)
*A61K 9/48* (2006.01)
*A61K 9/00* (2006.01)

(52) U.S. Cl.
CPC .......... *A61K 35/742* (2013.01); *A61K 9/0053* (2013.01); *A61K 9/48* (2013.01); *A61K 38/43* (2013.01); *A61P 1/00* (2018.01)

(58) Field of Classification Search
CPC .... A61K 35/742; A61K 38/43; A61K 9/0053; A61K 9/48; A61P 1/00
See application file for complete search history.

(56) References Cited

U.S. PATENT DOCUMENTS

| 2005/0100535 | A1* | 5/2005 | Farmer | A23L 33/135 |
| | | | | 424/93.46 |
| 2018/0338508 | A1* | 11/2018 | Majeed | A23L 2/52 |
| 2018/0353555 | A1* | 12/2018 | Majeed | A61K 35/742 |

OTHER PUBLICATIONS

Majeed et al., "Evaluation of the stability of Bacillus coagulans MTCC 5856 during processing and storage of functional foods", International J of Food Science, vol. 51, Issue 4, Apr. 2016 (Year: 2016).*

* cited by examiner

Primary Examiner — Ruth A Davis

(57) ABSTRACT

The present invention discloses a stable probiotic composition comprising *Bacillus coagulans* individually and/or in combination with multi-enzyme complex for the utilization of lactose and therapeutic management of lactose intolerance. It also discloses a method for the management of lactose intolerance using composition comprising *Bacillus coagulans* individually and/or in combination with multi-enzyme complex.

7 Claims, 5 Drawing Sheets

STABLE PROBIOTIC COMPOSITION FOR THE MANAGEMENT OF LACTOSE INTOLERANCE

BACKGROUND OF THE INVENTION

Field of the Invention

The invention in general relates to probiotic compositions. More specifically, the present invention relates to a stable probiotic composition comprising *Bacillus coagulans* individually and/or in combination with multi-enzyme complex for the utilization of lactose and therapeutic management of lactose intolerance.

Description of Prior Art

Lactase (beta-D-galactosidase, EC 3.2.1.23) is an endogenous enzyme which catalyses the hydrolysis of lactose to glucose and galactose. The enzyme is found in plants, animals, and microorganisms. In case of shortage of lactase in small intestine, lactose cannot be hydrolysed, leading to a condition called lactose intolerance. Lactose intolerance is the inability of adults and children to digest lactose, arising due to lactase deficiency, or hypolactasia. In some (rare) cases, individuals have congenital alactasia, a total absence of lactase caused by a genetic defect, which prevents them from being able to digest lactose from infancy. It is common for patients with inflammatory bowel disease to experience gastrointestinal symptoms after lactose ingestion, although the prevalence of lactase deficiency in this population has not been well studied. For this reason, majority of the world population encounters problems due to their consumption of foods containing high amount of lactose. Therefore, pre-processing of milk and dairy products with lactase to hydrolyse lactose is necessary in order to eliminate this disadvantage.

Lactase deficiency is a wide spread problem occurring in approximately 70% of the world's population. Consumption of milk by lactase deficient individuals results in lactose malabsorption leading to abdominal pain, diarrhea and flatulence. Lactose maldigestion is a common condition affecting up to 75% of the world's population due to the decline in the activity of lactase enzyme from the normal range.

This enzyme is responsible for cleavage of lactose, a disaccharide carbohydrate consisting of glucose and galactose. When the amount of ingested lactose exceeds the hydrolytic capacity of lactase in the intestine, undigested lactose is transported to the large intestine where it is fermented by the bacterial microflora, producing organic acids, carbon dioxide, and hydrogen. These by-products, along with the large amount of water osmotically drawn into the intestine, lead to the commonly known symptoms of abdominal pain, bloating, cramps, and flatulence. People with reduced ability to digest lactose can consume 0.5-7 g of lactose, which is equivalent to approximately 3 oz of milk, without experiencing symptoms of intolerance. Lactose maldigestion, therefore, does not necessarily lead to lactose intolerance. Lactase is produced naturally in human body; however, sometime the production is affected by certain factors. Further, excess intake of Lactose may also be responsible for lactose intolerance.

Recently probiotics gained the importance due to its various applications. They are live bacteria or yeast which supplements the gastrointestinal flora. Specifically strains belonging to *Bifidobacterium* and *Lactobacillus* are the most widely used probiotic bacteria for lactose intolerance as they are major groups of the gastrointestinal microbiota. Probiotics promote lactose digestion in lactose intolerance by increasing the overall hydrolytic capacity in the small intestine and increasing the colonic fermentation. Probiotics can decrease lactose concentration in fermented products, and increase active lactase enzyme entering the small intestine with the fermented products.

The use of probiotics for the management of lactose intolerance is already reported in the literature.
1. Sophia J. Oak & Rajesh Jha, The effects of probiotics in lactose intolerance: A systematic review, CRITICAL REVIEWS IN FOOD SCIENCE AND NUTRITION, 2018 Feb. 9:1-9
2. Probiotics show promise in tackling lactose intolerance, https://www.yogurtinnutrition.com/probiotics-promise-lactose-intolerance/ (accessed on 10 Jan. 2019)
3. Probiotics and Lactose Intolerance: The Facts https://www.optibacprobiotics.co.uk/professonals/blog/probotic-supplements-help-lactose-intolerance (accessed on 10 Jan. 2019)
4. The Effect of Probiotics on Lactose Intolerance (PLI) https://clinicaltrials.gov/ct2/show/NCT01593800 (accessed on 10 Jan. 2019)
5. Gozde Konuray and Zerrin Erginkaya, Potential Use of *Bacillus* coagulants in the Food Industry, Foods 13 Jun. 2018, 7, 92, pp 1-10

Similarly digestive enzymes and its various applications in lactose intolerance management, healthy gall bladder function, support immune system, breaking down of carbohydrates and lipids, etc. is well known in the state of art
1. haps://www.DigeZyme.com/DigeZyme/significance-of-enzymes/(accessed on 11 Jan. 2019)
2. Digestive Enzymes and IBS: Lactose Intolerance https://stephanieclairmont.com/digestive-enzymes-and-ibs-lactose-intolerance/(accessed on 11 Jan. 2019)
3. How Digestive Enzymes Can Help With Food Intolerance and More https://www.energeticnutrition.com/blog/2017/05/digestive-enzymes-can-help-food-intolerance/(Accessed on 11 Jan. 2019)
4. 7 Symptoms of Lactose Intolerance & Diet to Treat It https://draxe.com/symptoms-of-lactose-intolerance/(Accessed on 11 Jan. 2019)

Though probiotics have been reported for the management of lactose intolerance it is well known in the scientific art that biological effects of probiotics or products thereof are strain specific and cannot be generalised among genera, species and strains (Probiotics: In Depth/NCCIH U.S. Department of Health and Human Services, National Institutes of Health). Hence, there exists a need to find a superior probiotic strain with improved lactose utilisation potential. The present invention solves the above problem by disclosing the therapeutic potential of probiotic bacteria *Bacillus coagulans* for the management of lactose intolerance and increased utilization of lactose the invention also discloses a synergistic combination comprising probiotic bacteria *Bacillus coagulans* and multi-enzyme complex for increased lactose utilization.

It is the principle objective of the invention to disclose the use of probiotic bacteria *Bacillus coagulans* individually or in combination with multi-enzyme complex for the management of lactose intolerance.

It is another objective of the invention to disclose the use of probiotic bacteria *Bacillus coagulans* individually or in combination with multi-enzyme complex for the utilization of lactose.

The present invention solves the above mentioned objectives and provides further related advantages.

Deposit of Biological Material

The deposit of biological material *Bacillus coagulans* bearing accession number MTCC 5856, mentioned in the instant application has been made on 19 Sep. 2013 at Microbial Type Culture Collection & Gene Bank (MTCC), CSIR-Institute of Microbial Technology, Sector 39-A, Chandigarh—160036, India.

SUMMARY OF THE INVENTION

The present invention discloses the potential of probiotic bacteria *Bacillus coagulans* individually and/or in combination with multi-enzyme complex for the increased utilization of lactose. The invention further discloses a method for the management of lactose intolerance using composition comprising *Bacillus coagulans* individually and/or in combination with multi-enzyme complex.

Other features and advantages of the present invention will become apparent from the following more detailed description, which illustrate, by way of example, the principle of the invention.

DESCRIPTION OF THE MOST PREFERRED EMBODIMENTS

Figure 1A:
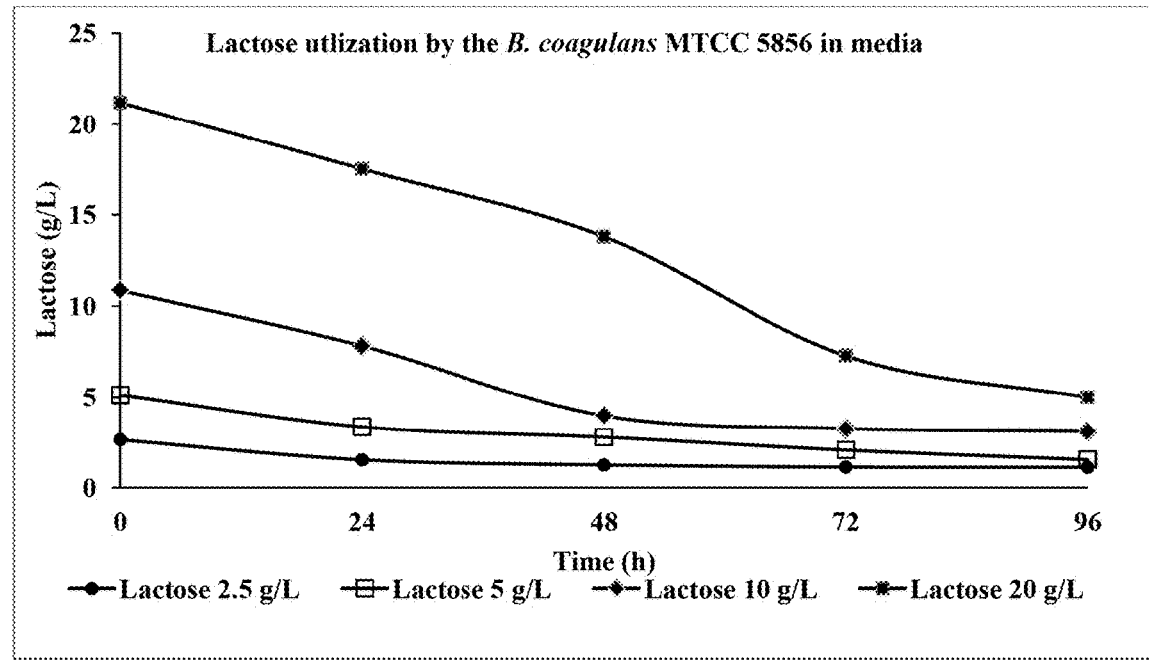
FIGS. 1*a* and 1*b* shows the graphical representation of utilization of lactose g/L (FIG. 1*a*) and percentage of reduction of lactose (FIG. 1*b*) in MRS media supplemented with 2.5, 5.0, 10 and 20 g/L by the probiotic strain *B. coagulans* MTCC 5856
Figure 1B:
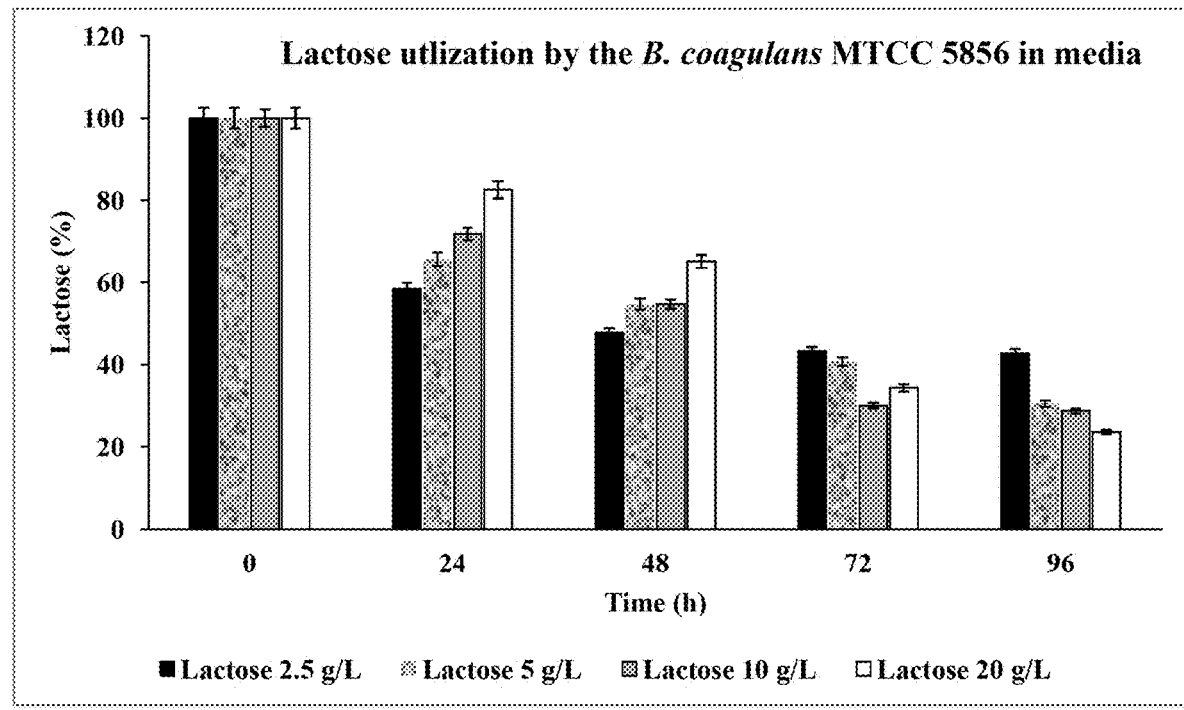
Figure 2:
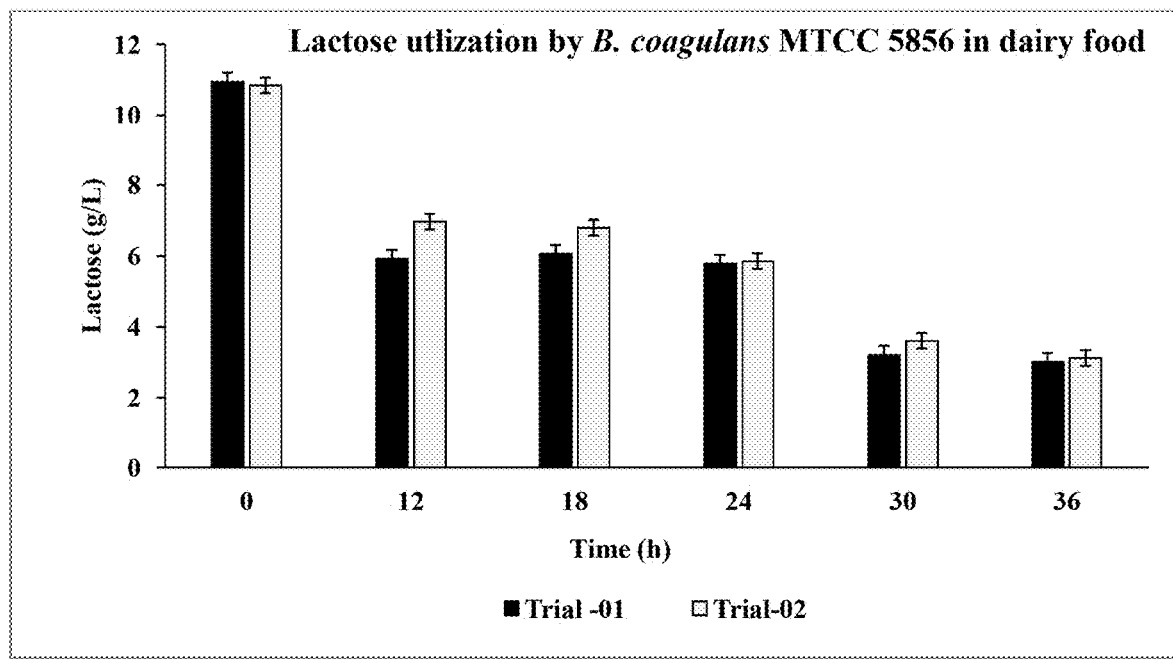
FIG. 2 shows the graphical representation of utilization of lactose in dairy food (skimmed milk) by *B. coagulans* MTCC 5856 after 36 h of fermentation
Figure 3:
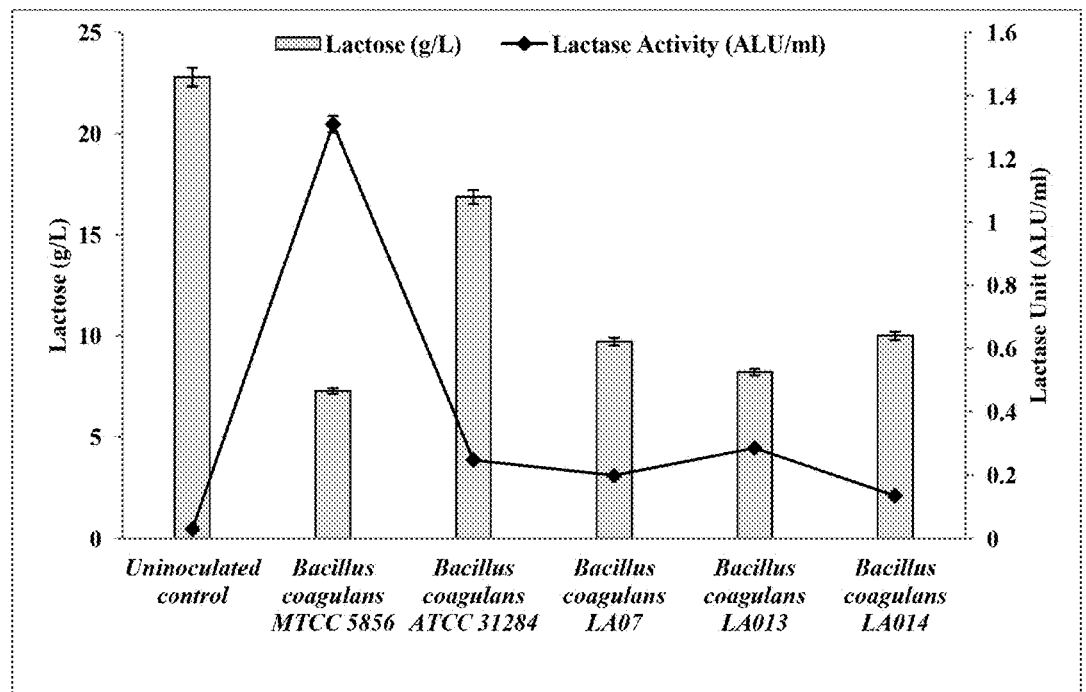
FIG. 3 shows the graphical representation of strain comparison of different strains of *B. coagulans* for lactose utilization and lactase enzyme production
Figure 4:
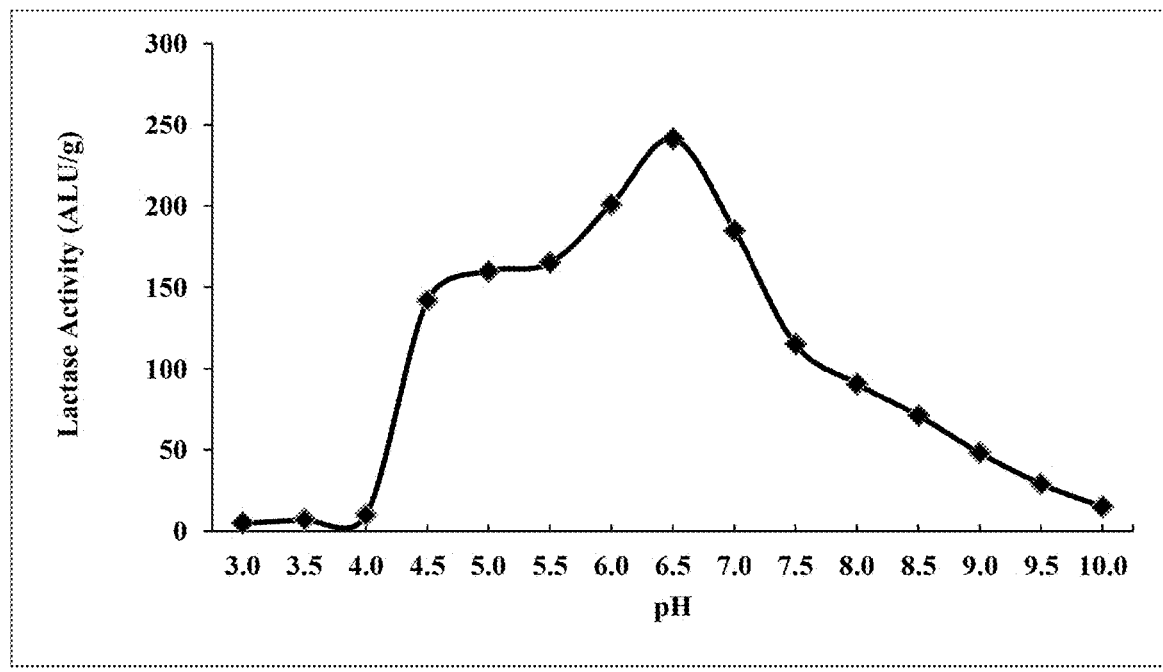
FIG. 4 shows the graphical representation of effect of pH on the lactase (β-galactosidase) enzyme activity from *Bacillus coagulans* MTCC 5856
Figure 5:
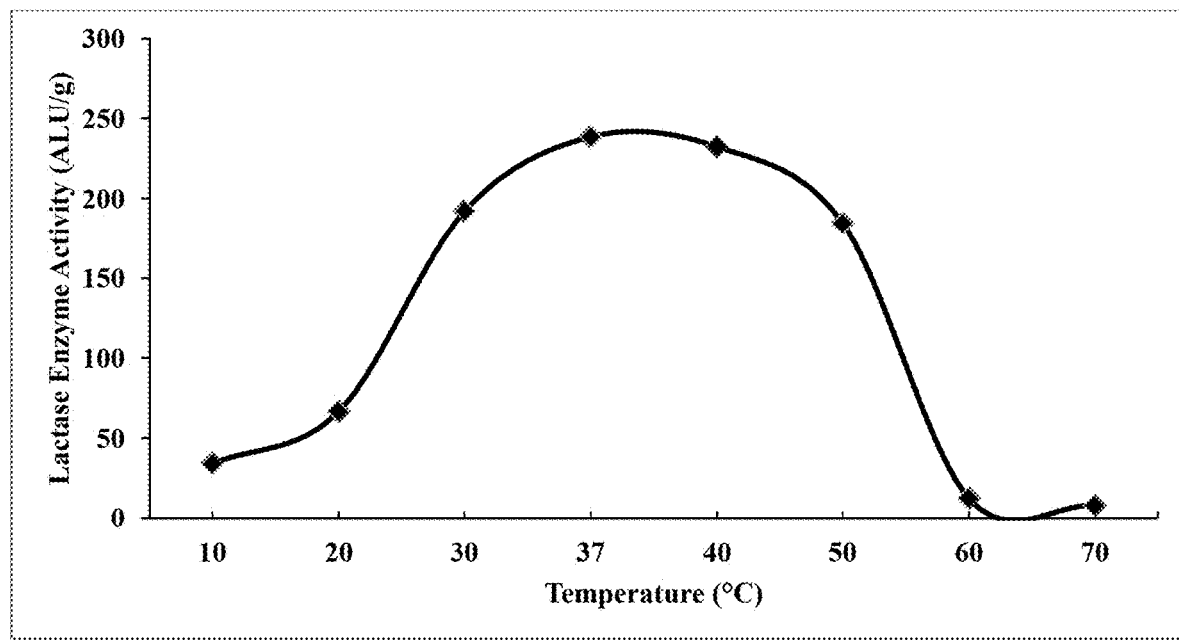
FIG. 5 shows the graphical representation of effect of temperature on the Lactase (β-galactosidase) enzyme activity from *Bacillus coagulans* MTCC 5856 was investigated at a temperature range from 10 to 70° C.
Figure 6:
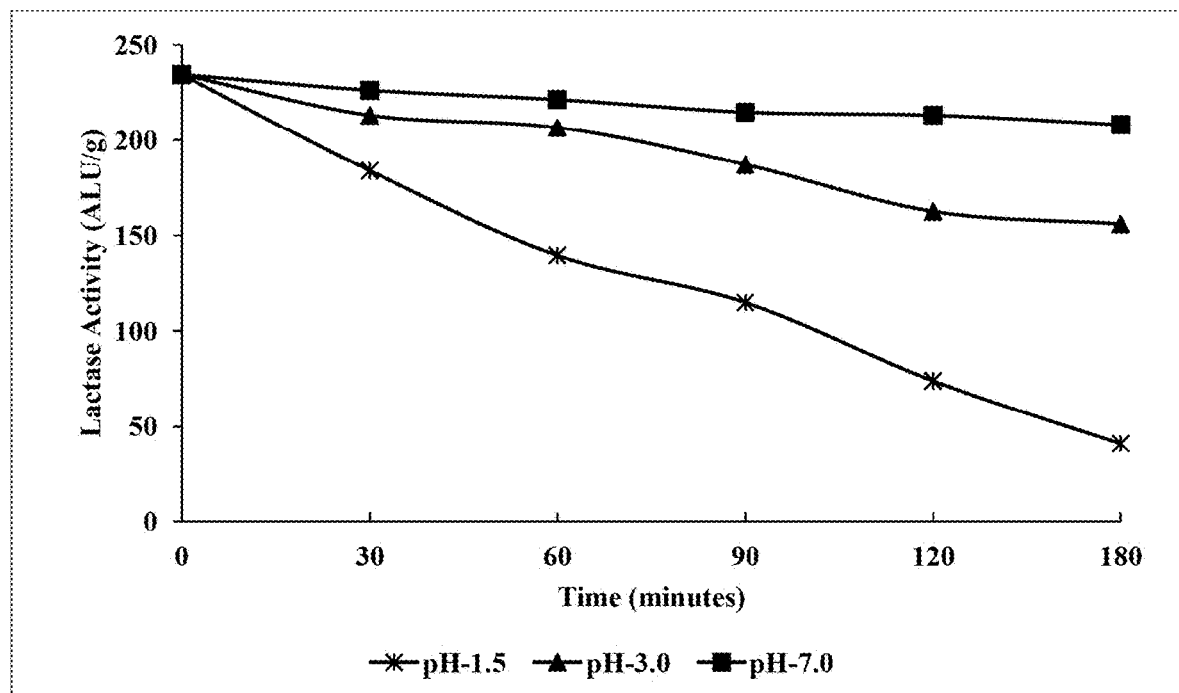
FIG. 6 shows the graphical representation of effect of gastric acid on the stability of lactase (β-galactosidase) activity was evaluated from the range of pH 1.5 to 7.0 for different time intervals up to 180 min
Figure 7:
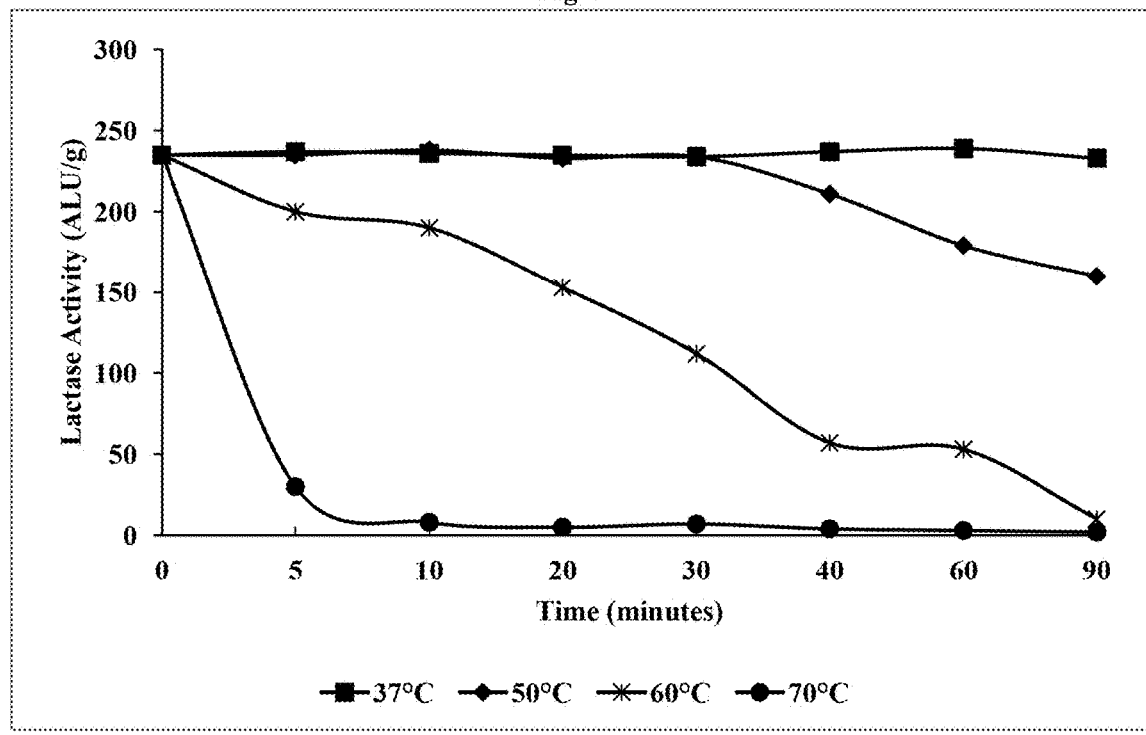
FIG. 7 shows the graphical representation of thermo stability of Lactase enzyme was evaluated from the range of 37 to 70° C.
Figure 8:
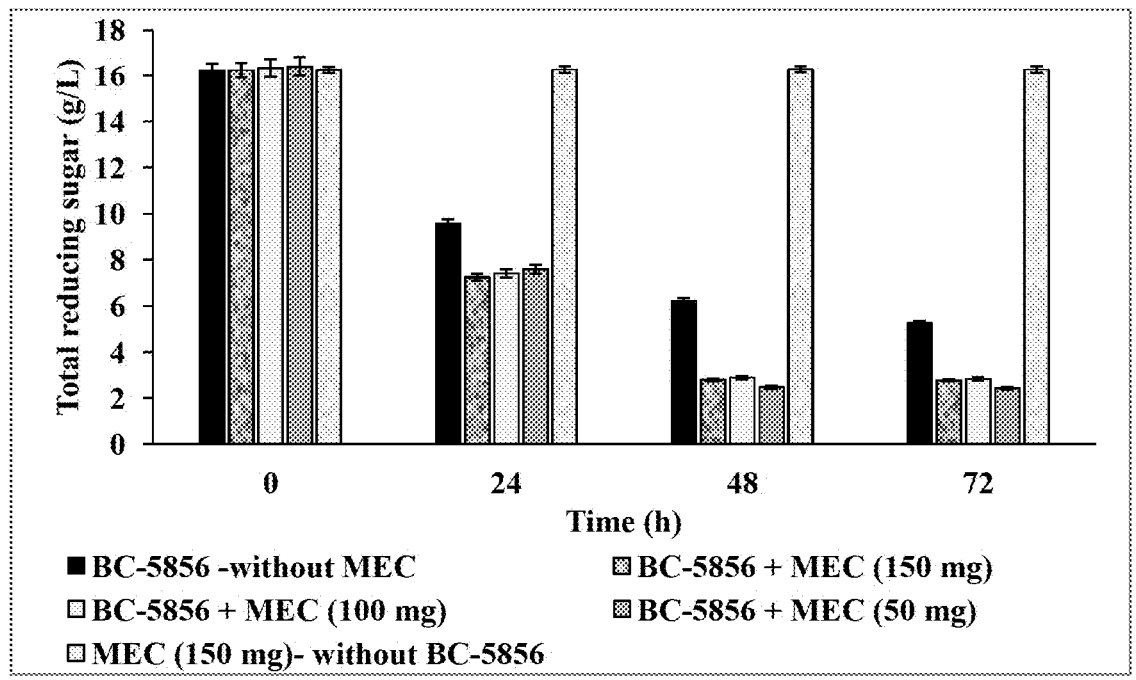
FIG. 8 shows the graphical representation of evaluation of utilization of Lactose by *B. coagulans* MTCC 5856 in media with multi enzyme complex (50, 100 and 150 mg) and without multi enzyme complex (as control) was performed
Figure 9:
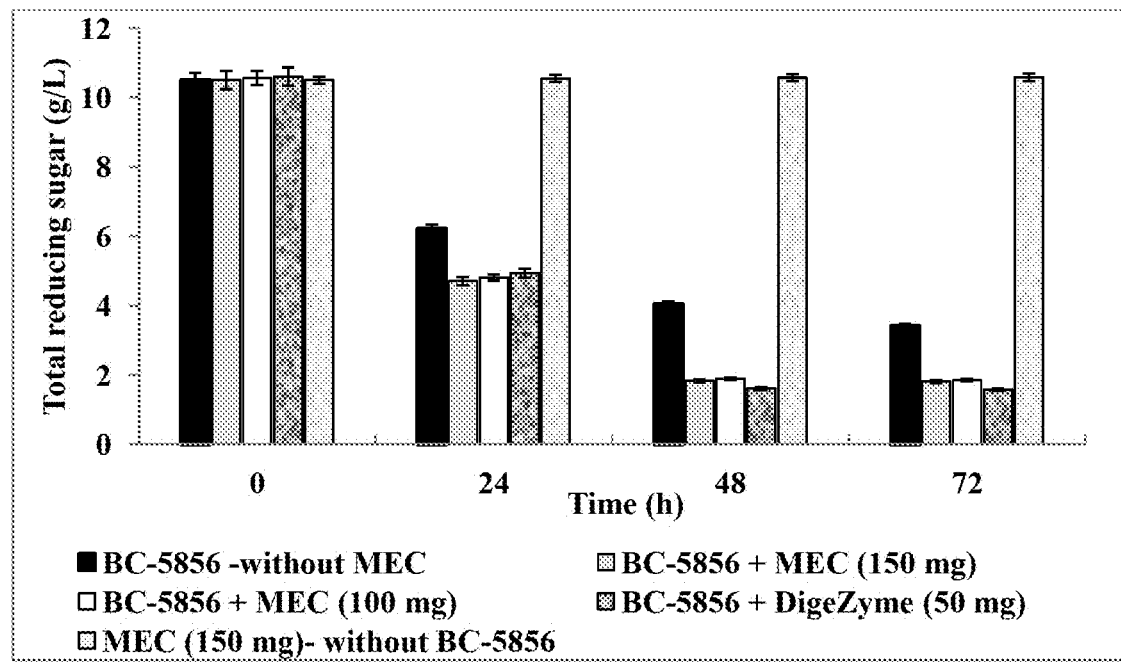
FIG. 9 shows the graphical representation of evaluation of utilization of lactose by *B. coagulans* MTCC 5856 in media containing skimmed milk with multi enzyme complex (50, 100 and 150 mg) and without multi enzyme complex (as control) was performed

In the most preferred embodiment, present invention relates to a method of increasing lactose utilization said method comprising step of bringing into contact foods containing lactose with probiotic bacteria *Bacillus coagulans* to bring about the effect of increased lactose utilization. In a related embodiment, *Bacillus coagulans* strain is specifically MTCC 5856. In another related embodiment, the foods containing lactose is selected from the group comprising milk, sour cream and buttermilk, butter, yogurt, cheese, ice cream, bread and baked goods like waffles, pancakes, biscuits, cookies and breakfast mixes, breakfast cereals, instant potatoes, soups, potato chips and corn chips and/or foodstuff wherein lactose is present.

In another most preferred embodiment, invention relates to a method of increasing lactose utilization, said method comprising step of bringing into contact foods containing lactose with probiotic bacteria *Bacillus coagulans* individually and/or in combination with multi-enzyme complex to bring about the effect of increased lactose utilization in synergistic manner. In yet another preferred embodiment, *Bacillus coagulans* strain is specifically MTCC 5856. In related embodiment, the food containing lactose is selected from the group comprising milk, sour cream and buttermilk, butter, yogurt, cheese, ice cream, bread and baked goods like waffles, pancakes, biscuits, cookies and breakfast mixes, breakfast cereals, instant potatoes, soups, potato chips and corn chips and/or foodstuff wherein lactose is present. In yet another related embodiment, the effective dose of *Bacillus coagulans* is $1\times10^6$ to $1\times10^{14}$ colony forming units (cfu) per unit dose. In further related embodiment, *Bacillus coagulans* is preferably $2\times10^9$ colony forming units (cfu) per unit dose. In yet another related embodiment, the multi-enzyme complex comprises of a) α-amylase: not less than 24000 DU/g, b) cellulase: not less than 1100 CU/g, c) lipase: not less than 200 FIP/g, d) lactase: not less than 4000 ALU/g and e) neutral or acid protease: not less than 6000 PC/a. In yet another related embodiment, the symptoms of lactose intolerance are selected from the group consisting of flatulence (wind), diarrhea, bloated stomach, stomach cramps and pains, stomach rumbling, nausea, feeling sick, borborygmi, and vomiting. In another related embodiment, lactose intolerance are selected from the group consisting of lactase deficiency, or hypolactasia, congenital alactasia, lactose ingestion, lactose malabsorption.

In yet another most preferred embodiment, invention relates to a method for the therapeutic management of lactose intolerance in mammals, said method comprising step of administering a composition comprising probiotic bacteria *Bacillus coagulans* individually and/or in combination with multi-enzyme complex to mammals in need of such therapy. In another preferred embodiment, mammal is human. In related embodiment, *Bacillus coagulans* strain is specifically MTCC 5856. In yet another related embodiment, the effective dose of *Bacillus coagulans* is $1\times10^6$ to $1\times10^{14}$ colony forming units (cfu) per unit dose. In further related embodiment, *Bacillus coagulans* is preferably $2\times10^9$ colony forming units (cfu) per unit dose. In yet another related embodiment, the symptoms of lactose intolerance are selected from the group consisting of flatulence (wind), diarrhea, bloated stomach, stomach cramps and pains, stomach rumbling, nausea, feeling sick, borborygmi, and vomiting. In another related embodiment, lactose intolerance are selected from the group consisting of lactase deficiency, or hypolactasia, congenital alactasia, lactose ingestion, lactose malabsorption. In yet another related embodiment, the multi-enzyme complex comprises of a) α-amylase: not less than 24000 DU/g, b) cellulase: not less than 1100 CU/g, c) lipase: not less than 200 FIP/g, d) lactase: not less than 4000 ALU/g and e) neutral or acid protease: not less than 6000 PC/g. In another related embodiment, composition containing *Bacillus coagulans* and multi-enzyme complex is formulated with pharmaceutically/nutraceutically acceptable excipients, adjuvants, bases, diluents, carriers, conditioning agents, bioavailability enhancers, antioxidants and preservatives and/or combined with other hepatoprotective compositions and administered orally in form of tablets, capsules, syrups, gummies, powders, suspensions, emulsions, chewables, candies or eatables.

The specific examples included herein below illustrate the aforesaid most preferred embodiments of the present invention.

EXAMPLES

Example 1: Utilization of Lactose by *Bacillus coagulans* MTCC 5856 in Media

*B. coagulans* MTCC 5856 was grown in media (Compositions: 10 g/l Soya Peptone, 6.5 g/l Yeast extract, 2.5 to 20 g/l Lactose, 1.0 g/l Dipotassium phosphate, 1.0 g/l Monopotassium phosphate, 0.3 g/l Magnesium sulfate and 0.3 g/l sodium chloride, pH 6.5) for 24 h. After 24 h of incubation, seed was transferred to fresh sterile media (Compositions: 10 g/l Soya Peptone, 6.5 g/l Yeast extract, 2.5 to 20 Lactose, 1.0 g/l Dipotassium phosphate, 1.0 Monopotassium phosphate, 0.3 g/l Magnesium sulfate and 0.3 g/l sodium chloride, pH 6.5) and incubated at 37° C. for 96 h with 180 rpm. After every 24 h of incubation, the fermented broth was checked for enzyme activity. Further, the supernatant was collected and carried out further for lactase enzyme assay. Lactase activity was determined as per standard method of Food Chemicals Codex (FCC) by using ortho-Nitrophenyl-β-galactoside (ONPG) as substrate (Institute of Medicine. 2003. Food Chemicals Codex: Fifth Edition. Washington, D.C.: The National Academies Press). Lactose content was determined as per the 3, 5-Dinitrosalicylic acid (DNSA) method (Miller, G. L. (1959). Use of dinitrosalicylic acid reagent for determination of reducing sugar. Analytical Chemistry, 31, 426-428).

Example 2: Utilization of Lactose by *Bacillus coagulans* MTCC 5856 in Dairy Foods (Skimmed Milk)

The utilization of lactose in dairy foods by *Bacillus coagulans* MTCC 5856 was evaluated by growing *Bacillus coagulans* MTCC 5856 in skimmed milk media. *Bacillus coagulans* MTCC 5856 was grown in media containing skimmed milk (20 g/L), soya peptone (5 g/L), calcium carbonate (0.05 g/L), Manganese sulfate (0.1 g/L), ammonium sulphate (1.46 g/L) using 2.5 L fermenter (Bioengineering AG Sagenrainstrasse, Wald, Switzerland). The fermented broth was checked for enzyme activity at different intervals. Further, the supernatant was collected and carried out further for lactase enzyme assay. Lactase activity was determined as per standard method of Food Chemicals Codex (FCC) by using ortho-Nitrophenyl-β-galactoside (ONPG) as substrate (Institute of Medicine. 2003. Food Chemicals Codex: Fifth Edition. Washington, D.C.: The National Academies Press). Lactose content was determined as per the 3, 5-Dinitrosalicylic acid (DNSA) method (Miller, G. L. (1959) by using lactose as standard. Use of dinitrosalicylic acid reagent for determination of reducing sugar. *Analytical Chemistry*, 31, 426-428).

Example 3: Lactase Enzyme Assay (O-Nitrophenol Beta-Galactosidase Enzyme Assay)

The supernatant collected from the fermented broth was tested for lactase activity. O-nitrophenyl-β-Dgalactopyranoside (ONPG) enzyme assay was used for testing the lactase activity. 4 ml of 3.7 mg/ml ONPG in acetate buffer-(Dilute 5.8 ml of glacial acetic acid in 1 L DM water, adjust the pH to 4.5) was pre-incubated for 10 min in 37° C. water bath, to that 1 ml of the sample (supernatant of broth and cell free extract) was added and further incubated at 37° C. for 15 min. To stop the reaction 1 ml of 1% $Na_2CO_3$ was added and then 8 ml of DM water was added. OD of samples was recorded at 420 nm. Lactase activity is expressed in ALU/ml or ALU/g. Lactase (ALU) "Acid Lactase unit"—One FCC Acid Lactase Unit (ALU) is defined as the quantity of enzyme that will liberate one micromole of o-nitrophenol per minute at 37° C. and a pH of 4.5. It is based on a 15-minute hydrolysis of an o-nitrophenol-beta D-galactopyranoside substrate.

Example 4: Effect of pH on the β-Galactosidase Activity from *Bacillus coagulans* MTCC 5856

The effect of pH on the lactase activity was determined by testing the enzyme activity at different pH values ranging from 3.0 to 10 using 0.05 M of the following buffer systems: sodium acetate (3.0, 3.5, 4.0, 4.5, 5.0, 5.5), sodium phosphate (pH 6.0, 6.5, 7.0, 7.5) and tris-HCl (pH 8.0, 8.5, 9.0, 9.5, 10). Lactase activity was determined as per standard method (FCC) by using ONPG as substrate (Institute of Medicine. 2003. Food Chemicals Codex: Fifth Edition. Washington, D.C.: The National Academies Press).

Example 5: Effect of Temperature on the β-Galactosidase Activity from *Bacillus coagulans* MTCC 5856

The effect of temperature on the activity of lactase was determined by performing the standard assay procedure at different temperatures ranging from 10 to 70° C. (10, 20, 30, 40, 50, 60, and 70° C.). Substrate was pre-incubated at the respective temperatures for 5 minutes followed by the enzyme activity determination as per the method of Food Chemicals Codex (FCC) using ortho-Nitrophenyl-β-galactoside (ONPG) as substrate.

Example 6: Gastric Acid and Thermo-Stability of the β-Galactosidase Activity from *Bacillus coagulans* MTCC 5856

The gastric stability of Lactase enzyme was evaluated by pre-incubating lactase enzyme produced by the *Bacillus coagulans* MTCC 5856 in buffer pH of 1.5 and 3.0. Samples were taken at 0, 30, 60, 90, 120 and 180 minutes of incubation. Lactase activity was determined as per standard method (FCC) by using ONPG as substrate (Institute of Medicine. 2003. Food Chemicals Codex: Fifth Edition. Washington, D.C.: The National Academies Press). Thermostabilty of lactase enzyme produced by the *Bacillus coagulans* MTCC 5856 was performed while incubating lactase enzyme in buffer at different temperature (50, 60 and 70° C.). Samples were taken at different time intervals (0, 5, 10, 20, 30, 40, 60 and 90 minutes). Lactase activity was determined as per standard method of Food Chemicals Codex (FCC) by using ortho-Nitrophenyl-β-galactoside (ONPG) as substrate (Institute of Medicine. 2003. Food Chemicals Codex: Fifth Edition. Washington, D.C.: The National Academies Press).

Example 7: Combination Study of *Bacillus coagulans* MTCC 5856 and Multi-Enzyme Complex for the Utilization of Lactose in Media and in Dairy Foods (Skimmed Milk)

*B. coagulans* MTCC 5856 was grown in media (Compositions: 10 g/l Soya Peptone, 6.5 g/l Yeast extract, 2.5 to 20 g/l Lactose, 1.0 g/l dipotassium phosphate, 1.0 g/l monopotassium phosphate, 0.3 g/l Magnesium sulfate and 0.3 g/l sodium chloride, pH 6.5) and various concentrations of multi-enzyme complex (50, 100 and 150 mg/L) were added after the media sterilization and along with *B. coagulans* MTCC 5856 and incubated at 37° C. for 72 h. After every 24 of incubation, lactose content was quantified by following DNSA method using lactose as standard. One group without multi-enzyme complex was also taken in this experiment. Another experiment was performed using media containing skimmed milk (20 g/L), soya peptone (5 g/L), calcium carbonate (0.05 g/L), Manganese sulfate (0.1 g/L), ammonium sulphate (1.46 g/L) and various concentrations of multienzyme complex (50, 100 and 150 mg/L) were added after the media sterilization and along with *B. coagulans* MTCC 5856 and incubated at 37° C. for 72 h. After every 24 of incubation, lactose content was quantified by following DNSA method using lactose as standard. One group without multi-enzyme complex was also taken in this experiment.

TABLE 1

Composition of the multi-enzyme complex (MEC)

| Sr. No. | Enzyme | Activity (Unit/g) |
|---|---|---|
| 1 | α-Amylase | 24000 DU |
| 2 | Neutral Protease | 6000 PC |
| 3 | Cellulase | 1100 CU |
| 4 | Lactase | 4000 ALU |
| 5 | Lipase | 200 FIP |

DU, Dextrinizing Unit; PU, Protease Unit; CU, Cellulase Unit; ALU, Acid Lactase Unit; FIP, Federation Internationale de Pharmaceutiques Unit Example 8: Formulations Containing *Bacillus coagulans* and Multi-Enzyme Complex for Lactose Intolerance

*Bacillus coagulans* and multi-enzyme complex is formulated with pharmaceutically/nutraceutically acceptable compositions with excipients, adjuvants, bases, diluents, carriers, conditioning agents, bioavailability enhancers, antioxidants and preservatives and/or combined with other hepatoprotective compositions and administered orally in form of tablets, capsules, syrups, gummies, powders, suspensions, emulsions, chewables, candies or eatables and administered for treatment of alcohol induced and drug hepatotoxicity. The following tables provide examples of different *Bacillus coagulans* and multi-enzyme complex compositions.

Tables 2-5 Provide illustrative examples of formulations containing *Bacillus coagulans* MTCC 5856 (LACTOSORE®) for the treatment/management of lactose intolerance.

TABLE 2

*Bacillus coagulans* tablet

| Active Ingredients |
|---|
| *Bacillus coagulans* MTCC 5856; 2 billion cfu (LACTOSORE ®) |
| Excipients |
| Microcystalline cellulose, Colloidal Silica, Magnesium Stearate |

* ®-Registered trade mark of Sabinsa Corporation, USA

TABLE 3

*Bacillus coagulans* capsule

| Active Ingredients |
|---|
| *Bacillus coagulans* MTCC 5856; 2 billion cfu (LACTOSORE ®) |
| Excipients |
| Maltodextrin |

* ®-Registered trade mark of Sabinsa Corporation, USA

TABLE 4

*Bacillus coagulans* drink mix

| Active ingredients |
|---|
| *Bacillus coagulans* MTCC 5856; 2 billion cfu (LACTOSORE ®) |
| Excipients |
| Maltodextrin, Taurin, Citric acid, Sucralose, Flavouring agent, Vitamin B6 and B12 |

* ®-Registered trade mark of Sabinsa Corporation, USA

TABLE 5

*Bacillus coagulans* + multi-enzyme complex (DigeZyme ®) tablet

| Active Ingredients |
|---|
| *Bacillus coagulans* MTCC 5856; 2 billion cfu (LACTOSORE ®) |
| Multi-enzyme complex (DigeZyme ®) |
| Excipients |
| Microcyscystalline cellulose, Colloidal Silica, Magnesium Stearate |

* ®-Registered trade mark or Sabinsa Corporation, USA

TABLE 6

*Bacillus coagulans* + multi-enzyme complex (DigeZyme ®) drink mix

| Active Ingredients |
|---|
| *Bacillus coagulans* MTCC 5856; 2 billion cfu (LACTOSORE ®) |
| Multi-enzyme complex (DigeZyme ®) |
| Excipients |
| Maltodextrin, Taurin, Citric acid, Sucralose, Flavouring agent, Vitamin B6 and B12 |

* ®-Registered trade mark of Sabinsa Corporation, USA

TABEL 7

Bacillus coagulans + multi-enzyme complex (DigeZyme ®) capsule

| Active Ingredients |
|---|
| *Bacillus coagulans* MTCC 5856; 2 billion cfu (LACTOSORE ®) |
| Multi-enzyme complex (DigeZyme ®) |
| Excipients |
| Maltodextrin |

* ®-Registerd trade mark of Sabinsa Corporation, USA

The above formulations are merely illustrative examples; any formulation containing the above active ingredient intended for the said purpose will be considered equivalent.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention. The scope of the invention is to be interpreted only in conjunction with the appended claims.

We claim:

1. A method of increasing utilization of lactose by probiotic bacteria *Bacillus coagulans* MTCC5856 from a food containing lactose, said method comprising a step of bringing into contact said food containing lactose with an effective dose of a composition comprising probiotic bacteria *Bacillus coagulans* MTCC5856 and enzymes comprising α-amylase, cellulase, lipase, lactase and neutral or acid protease, to bring about the effect of increasing utilization of lactose by *Bacillus coagulans* MTCC5856 by metabolizing the lactose in food in synergistic manner.

2. The method as in claim 1, wherein the effective dose of *Bacillus coagulans* is $1\times10^6$ to $1\times10^{14}$ colony forming units (cfu) per unit dose.

3. The method as in claim 1, wherein the effective dose of *Bacillus coagulans* is $2\times10^9$ colony forming units (cfu) per unit dose.

4. The method according to claim 1, wherein the enzymes comprise a) α-amylase: not less than 24000 DU/g, b) cellulase: not less than 1100 CU/g, c) lipase: not less than 200 FIP/g, d) lactase: not less than 4000 ALU/g and e) neutral or acid protease: not less than 6000 PC/g.

5. The method according to claim 1, wherein the food containing lactose is selected from the group consisting of milk, sour cream, buttermilk, butter, yogurt, cheese, ice cream, bread, baked goods, waffles, pancakes, biscuits, cookies, breakfast mixes, breakfast cereals, instant potatoes, soups, potato chips and corn chips.

6. The method as in claim 1, wherein the increasing utilization of lactose by *Bacillus coagulans* MTCC5856 and enzyme blend is effective in managing symptoms of lactose intolerance, selected from the group consisting of flatulence, diarrhea, bloated stomach, stomach cramps and pains, stomach rumbling, nausea, borborygmi, and vomiting.

7. The method as in claim 6, wherein symptoms of lactose intolerance occurs in conditions selected from the group consisting of lactase deficiency, congenital alactasia, lactose ingestion, and lactose malabsorption.

* * * * *